United States Patent
Guennouni et al.

(10) Patent No.: US 7,307,180 B2
(45) Date of Patent: Dec. 11, 2007

(54) METHOD OF PREPARING HALOGENOALKYLDIALKYL CHLOROSILANE

(75) Inventors: Nathalie Guennouni, Irigny (FR); Kamel Ramdani, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 10/534,246

(22) PCT Filed: Jul. 21, 2003

(86) PCT No.: PCT/FR03/02301

§ 371 (c)(1), (2), (4) Date: Feb. 15, 2006

(87) PCT Pub. No.: WO2004/016628

PCT Pub. Date: Feb. 26, 2004

(65) Prior Publication Data
US 2006/0167296 A1 Jul. 27, 2006

(30) Foreign Application Priority Data

Aug. 9, 2002 (FR) .................................. 02 10146
Jan. 13, 2003 (FR) .................................. 03 00284

(51) Int. Cl.
C07F 7/00 (2006.01)
(52) U.S. Cl. ...................................... 556/473; 556/479
(58) Field of Classification Search ................ 556/466, 556/479, 473
See application file for complete search history.

(56) References Cited

U.S. PATENT DOCUMENTS 4,272,288 A * 6/1981 Dessau ........................ 75/426
6,359,161 B2 * 3/2002 Tonomura et al. .......... 556/479

FOREIGN PATENT DOCUMENTS

EP 1 156 052 A 11/2001

* cited by examiner

Primary Examiner—Yvonne Eyle
Assistant Examiner—Sudhakar Katakam
(74) Attorney, Agent, or Firm—Buchanan, Ingersoll & Rooney, PC

(57) ABSTRACT

A process for the preparation of a haloalkyldialkylchlorosilane is provided, wherein at the end of a hydrosilylation reaction, the product is recovered and iridium is recovered, the iridium being found in its original form of catalyst or in a converted form, the recovery of the iridium taking place under the following conditions a), b) and c): a) the recovery of the iridium is carried out: 1. either directly on the reaction medium at the end of the reaction, 2. or on the liquid distillation residue, including the byproducts and the iridium or its derivatives, as is obtained after distillation of the reaction medium in order to separate therefrom the product of formula (I), b) the iridium is recovered by bringing the reaction medium or the distillation residue into contact with an effective amount of carbon black which adsorbs the iridium, and c) the carbon black is separated from the iridium for the purpose of recovering the iridium.

10 Claims, 1 Drawing Sheet

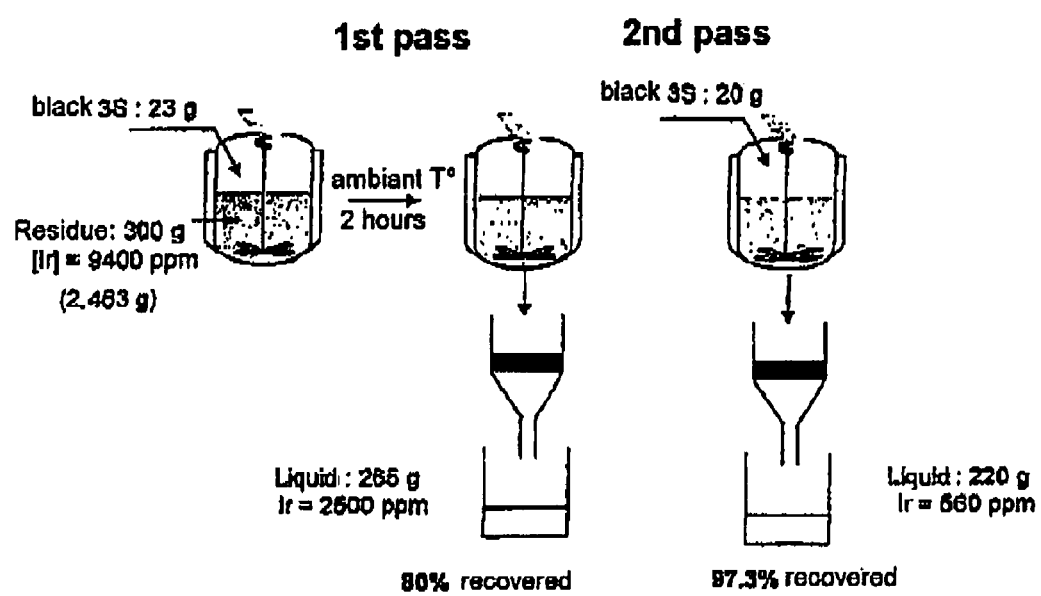

METHOD OF PREPARING HALOGENOALKYLDIALKYL CHLOROSILANE

The present invention relates to a process for the preparation of haloalkyldialkylchlorosilane.

More particularly, the present invention relates to a process for the preparation of 3-chloropropyldimethylchlorosilane by hydrosilylation of dimethylhydrochlorosilane using allyl chloride and a catalyst based on a platinum ore metal and recovery of said metal.

In this type of reaction, the amounts of platinum ore metal involved are often high for the purpose of obtaining a satisfactory yield. This amount of metal catalyst is generally greater than 30 ppm, calculated with respect to the total weight of the reaction mixture. In order for the process to remain economically advantageous, it is desirable to be able to recover the platinum ore metal in order to be able to reuse it as catalyst.

The present invention provides a process for the preparation of a haloalkyldialkylchlorosilane of the above type comprising a stage of recovery of the catalytic metal.

BRIEF DESCRIPTION OF THE DRAWING

FIG. 1 shows an exemplary process of recovering iridium using carbon black powder as discussed in Example 7.

Specifically, the present invention relates to a process for the preparation of a haloalkyldialkylchlorosilane of formula (I):

$$\text{Hal-}(R^2R^3)\text{Si}—(CH_2)_s\text{-Hal}$$

by the hydrosilylation reaction of a reaction medium comprising a silane of formula (II):

$$\text{Hal-}(R^2R^3)\text{Si}—H$$

and an alkenyl halide of formula (III):

$$CH_2=CH—(CH_2)_{s-2}\text{Hal}$$

in the presence of a catalytically effective amount of a hydrosilylation catalyst based on a platinum ore metal, in which formulae:
the symbol Hal represents a halogen atom chosen from chlorine, bromine and iodine atoms, the chlorine atom being preferred,
the symbols $R^2$ and $R^3$, which are identical or different, each represent a monovalent hydrocarbon group chosen from a linear or branched alkyl radical having from 1 to 6 carbon atoms and a phenyl radical, and
s represents an integer between 2 and 10 inclusive, said process being characterized in that, at the end of the hydrosilylation reaction, the product of formula (I) formed is recovered and the catalytic platinum ore metal is recovered, said metal being found in its original form of catalyst or in a converted form, the recovery of said catalytic metal taking place under the following conditions a), b) and c):
a) the recovery of the catalytic metal is carried out:
  1. either directly on the reaction medium at the end of the reaction,
  2. or on the liquid distillation residue, comprising the byproducts and the platinum ore metal or its derivatives, as is obtained after distillation of the reaction medium in order to separate therefrom the product of formula (I),
b) the catalytic metal is recovered by bringing the reaction medium or the distillation residue into contact with an effective amount of a solid substance which adsorbs the platinum ore metal, and
c) the adsorbent is separated from the platinum ore metal for the purpose of recovering said metal.

The platinum ore metal is chosen from platinum, iridium, palladium, rhodium, ruthenium and osmium, the preferred metal being iridium. In the context of this preferred arrangement, suitable Ir-based catalysts are in particular:

$[IrCl(CO)(PPh_3)_2]$
$[Ir(CO)H(PPh_3)_3]$
$[Ir(C_8H_{12})(C_5H_5N)P(C_6H_{11})_3]PF_6$
$[IrCl_3].nH_2O$
$H_2[IrCl_6].nH_2O$
$(NH_4)_2IrCl_6$
$Na_2IrCl_6$
$K_2IrCl_6$
$KIr(NO)Cl_5$
$[Ir(C_8H_{12})_2]^+BF_4^-$
$[IrCl(CO)_3]_n$
$H_2IrCl_6$
$Ir_4(CO)_{12}$
$Ir(CO)_2(CH_3COCHCOCH_3)$
$Ir(CH_3COCHCOCH_3)$
$IrBr_3$
$IrCl_3$
$IrCl_4$
$IrO_2$
$(C_6H_7)(C_8H_{12})Ir$.

In the context of the even more preferred arrangement mentioned above, other Ir-based catalysts which are even better suited are taken from the group of the iridium complexes of formula:

$$[Ir(R^4)Hal]_2 \qquad (IV)$$

where:
the symbol $R^4$ represents an unsaturated hydrocarbon ligand comprising at least one C=C double bond and/or at least one C≡C triple bond, it being possible for these unsaturated bonds to be conjugated or non-conjugated, said ligand being linear or cyclic (mono- or polycyclic), having from 4 to 30 carbon atoms, having from 1 to 8 ethylenic and/or acetylenic unsaturations and optionally comprising one or more heteroatoms, such as, for example, an oxygen atom and/or a silicon atom;
the symbol Hal is as defined above.

Mention will be made, as examples of iridium complexes of formula (IV) which are even better suited, of those in the formula of which:
the symbol $R^4$ is chosen from 1,3-butadiene, 1,3-hexadiene, 1,3-cyclohexadiene, 1,3-cyclooctadiene, 1,5-cyclooctadiene, 1,5,9-cyclododecatriene and norbornadiene, and the following compounds of formulae:

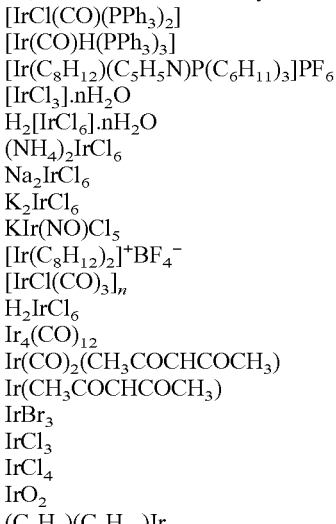

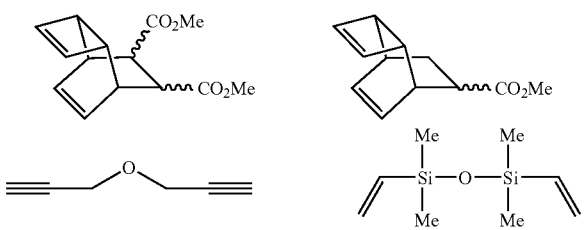

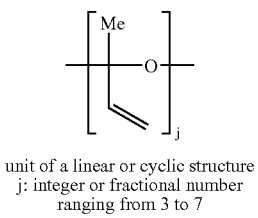

unit of a linear or cyclic structure
j: integer or fractional number
ranging from 3 to 7

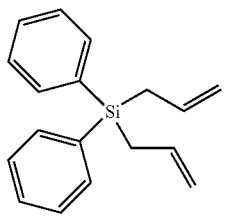

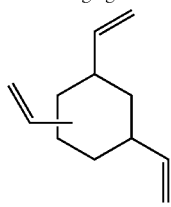

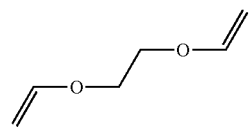

the symbol Hal represents a chlorine atom.

Mention will be made, as specific examples of iridium complexes which are even better suited, of the following catalysts:
di-μ-chloro-bis(divinyltetramethyldisiloxane)diiridium,
di-μ-chloro-bis(η-1,5-hexadiene)diiridium,
di-μ-bromo-bis(η-1,5-hexadiene)diiridium,
di-μ-iodo-bis(η-1,5-hexadiene)diiridium,
di-μ-chloro-bis(η-1,5-cyclooctadiene)diiridium,
di-μ-bromo-bis(η-1,5-cyclooctadiene)diiridium,
di-μ-iodo-bis(η-1,5-cyclooctadiene)diiridium,
di-μ-chloro-bis(η-2,5-norbornadiene)diiridium,
di-μ-bromo-bis(η-2,5-norbornadiene)diiridium,
di-μ-iodo-bis(η-2,5-norbornadiene)diiridium.

Without departing from the scope of the present invention, use may be made, in addition to the catalyst based on a platinum ore metal, of at least one hydrosilylation reaction promoter.

Mention may be made, as optional promoter(s), of: a compound which can exhibit, for example, the form of a ligand or of an ionic compound, taken in particular from the group formed by: an organic peroxide; a carboxylic acid; a carboxylic acid salt; a tertiary phosphine; a phosphite, such as, for example, an optionally mixed alkyl and/or aryl phosphite; an amine; an amide; a linear or cyclic ketone; a trialkylhydrosilane; benzotriazole; phenothiazine; a compound of trivalent metal-$(C_6H_5)_3$ type where metal=As, Sb or P; a mixture of amine or of cyclohexanone with an organosilicon compound comprising one or more ≡Si—H group(s); the compounds $CH_2$=CH—$CH_2$—OH or $CH_2$=CH—$CH_2$—$OCOCH_3$; a lactone; a mixture of cyclohexanone with triphenylphosphine; or an ionic compound, such as, for example, an alkali metal or imidazolinium nitrate or borate, a phosphonium halide, a quaternary ammonium halide or a tin(II) halide.

The optional promoter(s), when one (or more) thereof is (are) used, is (are) generally introduced at the beginning of the reaction, either in the form under which it (they) is (are) normally found or in the form of a premix based on: promoter(s)+catalyst(s); or promoter(s)+all or part of the diorganohalosilane of formula (II); or promoter(s)+all or part of the alkenyl halide of formula (III).

The catalyst can be used, and this is another preferred arrangement, in a homogeneous liquid medium, as is disclosed in JP-B-2 938 731 and EP-A-1 156 052. In this context, the reaction can be carried out either continuously or semicontinuously or batchwise. At the end of the operation, the product of formula (I) formed is recovered and the catalytic platinum ore metal is recovered, as indicated above.

According to the present invention, the reaction mixture or the liquid distillation residue is brought into contact with an effective adsorbing amount of a solid adsorbent agent.

The solid adsorbent is generally provided in the form of a powder, extrudate or granule or grafted to a support, such as cellulose, for example.

The use is more especially recommended, as solid adsorbent, of carbon black; active charcoals; molecular sieves which are generally synthetic zeolites or metal aluminosilicates or silicates; silicas; activated aluminas; diatomite- and pearlite-based adsorbent fillers; activated and ground clays based on bentonite and on attapulgite; ion-exchange resins; or resins of amberlite or amberlyst type.

Adsorption can advantageously be carried out batchwise by bringing an adsorbent solid of the powder or granule type into contact with the reaction mixture or the distillation residue. Adsorption can advantageously also be carried out continuously by bringing an adsorbent solid present in a column or a fixed bed or a cartridge into contact with the reaction mixture or the distillation residue. The contact time can vary from 5 minutes to 10 hours, preferably between 30 minutes and 7 hours, under batchwise conditions. The temperature can vary from 5 to 150° C., preferably from 10 to 30° C.

The amount of adsorbent used for active charcoals, molecular sieves, silicas, aluminas and inorganic adjuvants is closely related, first, to the specific adsorption capacity relating to each of the adsorbents which it is possible to use in the context of the invention and, secondly, to the processing parameters, such as the temperature and the presence or absence of a solvent.

The adsorption capacity (q) is expressed as number of moles of platinum ore metal adsorbed per kilogram of adsorbent used. This amount q is generally between 0.01 and 5. In the case where the adsorbent is an ion-exchange resin, the resin is characterized by an exchange capacity value which is specific for each grade of resin and which relates to the functionality carried by this resin. This exchange capacity is generally expressed in meq/g for a dry product and in meq/ml with regard to a wet product. These resins will preferably be used in such a way that the molar ratio of the functional group carried by the resin to the platinum ore metal present in the solution to be treated is between 1 and 30, preferably between 1 and 15 and more particularly between 1 and 5.

The absorption stage can be carried out at atmospheric pressure or under reduced pressure and optionally in the presence of a solvent which is inert with respect to the hydrogen halide HHal present in trace amounts in the medium (in the case where the residue is not hydrolyzed as indicated below). It is recommended to use alkanes (preferably $C_6$ and $C_7$ alkanes), aromatic solvents (toluene, xylene or chlorobenzene) and ketones. The amount of alkenyl halide of formula (III) used is preferably from 1 to 2 mol per 1 mol of silane of formula (II). With regard to the amount of catalyst(s) (i), expressed as weight of platinum ore metal, it lies in the range from 1 to 10 000 ppm, preferably from 10 to 2000 ppm and more preferably from 20 to 1000 ppm, based on the weight of silane of formula (II).

The solid adsorbent, at the surface of which the catalytic metal is adsorbed, is separated from the reaction medium or from the distillation residue by any suitable means for liquid/solid separation, such as filtration, centrifuging or settling. The metal is subsequently separated from the adsorbent by any physical/chemical means compatible with said adsorbent.

In the case where the adsorption stage is carried out on the distillation residue, the process, according to a preferred alternative embodiment, additionally comprises, after the stage of distillation of the reaction medium, an additional stage in which the liquid residue is brought into contact with water optionally in the presence of an organic solvent which is inert with regard to HHal formed, for the purposes of obtaining an aqueous phase and an organic phase and of hydrolyzing said residue, which makes it possible thus to achieve the objective of rendering the reactive residue inert.

The reaction carried out consists in converting all the Si—Cl functional groups present in the distillation residue to silanol Si—OH and siloxane Si—O—Si functional groups by performing, by bringing an aqueous solution into contact with the distillation residue, the chemical reactions:

Si-Hal+$H_2O$→Si—OH+HHal

Si—OH+Si-Hal→Si—O—Si+HHal and

Si—OH+Si—OH→Si—O—Si+$H_2O$

Hydrolysis can be carried out in an acidic or basic medium. If the reaction is carried out in an acidic medium, the aqueous solution used as reactant may be preacidified (with HHal, for example) or may be composed solely of demineralized water. The pH of the solution then changes during the reaction to values below 7. In this case, it is possible to neutralize the aqueous phase at the end of hydrolysis by adding a base. Hydrolysis is preferably carried out in a basic medium so that all the HHal is removed. It is recommended to run the residue onto a heel of aqueous solution. Hydrolysis can be carried out at temperatures from −15° C. to 80° C. As the reaction is exothermic, the residue is preferably run in at moderate temperatures between −10 and 30° C. Control of the temperature may prove to be necessary. After the residue has finished being run in, the medium obtained is a two-phase medium, composed of an organic phase and of an aqueous phase.

Preferably, the water is added in an amount sufficient for the HHal formed not to be at saturation in the aqueous phase.

Preferably, the product of formula (I) is 3-chloropropyldimethylchlorosilane, the product of formula (II) is dimethylhydrochlorosilane and the product of formula (III) is allyl chloride. In this case, the hydrogen halide formed is HCl.

The following examples illustrate the invention without limiting the scope thereof.

In the examples below, a hydrosilylation reaction of dimethylhydrochlorosilane with allyl chloride in the presence of 500 ppm of di-μ-chloro-bis(η-1,5-cyclooctadiene) diiridium with respect to the weight of dimethylhydrochlorosilane is first of all carried out. The dimethylhydrochlorosilane is added dropwise over 7 hours at a temperature of 38° C. to the reaction medium in a reactor equipped with a stirrer, a reflux condenser and a thermometer. The final medium thus obtained constitutes the reaction medium which is treated in some of the following examples. The 3-chloropropyldimethylchlorosilane is separated from the reaction medium by distillation and a liquid distillation residue comprising the catalyst remains; it is this distillation residue which is treated in some of the following examples.

EXAMPLE 1

Recovery of the Iridium with 2% by Weight of Carbon Black with Regard to a Distillation Residue which is Neither Diluted nor Hydrolyzed 208.85 g of distillation residue comprising 1.2% by weight of iridium are introduced into a 1 liter four-necked flask equipped with a mechanical stirrer and in which an argon atmosphere is present. The reaction medium is stirred and heated to 60° C.

4.235 g of carbon black 2S, sold by Ceca, are then added and the temperature conditions are maintained for 1 hour. The medium is then filtered under argon pressure on a stainless steel filter (0.5 μm). The oil corresponding to the filtrate and the cake are recovered and analyzed by elemental analysis.

The results obtained are collated in Table 1 below:

TABLE 1

| Examples | | Ir** | C | H | Cl | Si | Σ |
|---|---|---|---|---|---|---|---|
| 1 | Oil before treatment | 1.2 | 39.3 | 7.8 | 33.1 (32.3)* | 17.6 | 99.8 |
| 1 | Oil, treatment with 2% by weight of carbon black and after filtration | 0.83 | 40.4 | 8.2 | 32.2 (30.6)* | 18.2 | 99.8 |
| 1 | Cake after filtration resulting from the 2% treatment | 8.0 | 56.4 | 4.9 | 15.42 (14.1)* | 9.2 | 93.9 |

**The values shown represent the concentration by weight of Ir in the medium under consideration
Rq: values rounded to one decimal place due to the instability of the compounds
*second measurement The efficiency is 30.8%.

The capacity of the black for this concentration of 3.07 mol of Ir/kg of black 2S.

EXAMPLE 2

Recovery of the Iridium with 5% by Weight of Carbon Black with Regard to a Distillation Residue which is Neither Diluted nor Hydrolyzed 194.2 g of distillation residue identical to that used in Examples 1 to 3 and comprising 1.2% by weight of iridium are introduced into a 1 liter four-necked flask equipped with a mechanical stirrer and in which an argon atmosphere is present. The reaction medium is stirred and heated to 60° C.

9.75 g of carbon black 2S (Ceca) are then introduced and the temperature conditions are maintained for 1 hour. The medium is then filtered under argon pressure on a stainless steel filter. The oil corresponding to the filtrate and the cake are recovered and analyzed by elemental analysis.

The results obtained are collated in Table 2 below:

TABLE 2

| Examples | | Ir(**) | C | H | Cl | Si | Σ |
|---|---|---|---|---|---|---|---|
| 2 | Oil before treatment | 1.2 | 39.3 | 7.8 | 33.1 (32.3)* | 17.6 | 99.8 |
| 2 | Oil, treatment with 5% by weight of carbon black and after filtration | 0.63 | 38.7 | 7.8 | 31.8 (30.8)* | 19.6 | 98.5 |

TABLE 2-continued

| Examples | Ir(**) | C | H | Cl | Si | Σ |
|---|---|---|---|---|---|---|
| 2 Cake after filtration resulting from the 5% treatment | 6.2 | 55.6 | 4.8 | 19.0 (18.6)* | 9.3 | 94.9 |

Rq: values rounded to one decimal place due to the instability of the compounds
*second measurement The efficiency is 47.5%.

The capacity of the black for this concentration of 1.243 mol of Ir/kg of black 2S.

EXAMPLE 3

Recovery of the Iridium with Carbon Black with Regard to a Distillation Residue which has been Diluted and Hydrolyzed The Distillation Residue Used is Hydrolyzed Beforehand in an Acidic Medium:

The distillation residue identical to that used in Examples 1 to 6 (50.12 g) is introduced at a flow rate of 2 ml/min via a peristaltic pump onto a very vigorously stirred (400 rev/min) heel of demineralized water (500.7 g) in a one liter three-necked flask equipped with a mechanical stirrer, a temperature probe and a septum. The temperature of the medium increases, changing from 21° C. to 25.3° C. when the residue has finished being run in. Stirring is maintained for 1 h 30. The combined medium is transferred to a separating funnel and the organic phase is recovered after addition of 2×250 ml of toluene (phase A).

A fraction of this solution is evaporated (50° C./70 mbar). A fluid oil with a deep black color is recovered and analyzed:
  % Ir: 0.55%
  $^{29}$Si NMR: absence of functional group of SiCl type
  SC (solids content): 6.61%

Treatment with 2% of Carbon Black 2S:

A fraction of the toluene phase (phase A) is recovered (191.88 g) and introduced into a single-necked flask. 3.84 g of carbon black 2S are introduced and the round-bottomed flask is then placed on a rotary evaporator at 60° C. and at atmospheric pressure. The carbon black is then recovered by filtration under pressure on a stainless steel filter (0.5 μm). The cake is washed with 150 ml of toluene and then partially dried by passing nitrogen over the cake.

The organic phase is evaporated. The oil obtained is orangey and comprises 0.18% of iridium. A weight of 5.95 g of cake is recovered. It comprises 1.27% of iridium.

The efficiency is 67.3%.

The capacity of the black for this concentration of 94.59× $10^{-3}$ mol of Ir/kg of black 2S.

Double Treatment with 5% of Carbon Black 2S:

A fraction of the toluene phase (phase A) is recovered (157.65 g) and introduced into a single-necked flask. 7.88 g of carbon black 2S are introduced and the round-bottomed flask is then placed on a rotary evaporator at 60° C. and at atmospheric pressure. The black is then recovered by filtration under pressure on a stainless steel filter (0.5 μm). The cake is washed with 150 ml of toluene and then partially dried by passing nitrogen over the cake.

The organic phase is stored. 10.27 g of cake are recovered. It comprises 0.64% of iridium.

A second treatment is carried out on the organic phase. 7.88 g of carbon black 2S are introduced into the single-necked flask comprising the organic phase and the medium is heated on a rotary evaporator at 60° C. for 1 hour. The medium is then filtered. The organic phase recovered after filtration (conditions identical to the preceding conditions) is evaporated. A very slightly yellowish and clear fluid oil is recovered. It comprises 355 ppm of iridium.

The carbon black recovered is partially dried. It comprises 865 ppm of iridium.

The efficiency is 93.5%.

The capacity of the black for this concentration of 1.892× $10^{-2}$ mol of Ir/kg of black 2S.

EXAMPLE 4

Recovery of the Iridium with Carbon Black 2S (Ceca) with Regard to a Distillation Residue which has been Diluted and Hydrolyzed Hydrolysis is carried out in a basic medium.

The starting material used is the distillation residue identical to that of the preceding examples but in the form of a solution comprising between 0.71-0.72% and 0.78-0.82% of iridium and with an HCl (releasable) assay of 0.104 g of HCl/g of solution.

Hydrolysis is carried out by running this solution onto a sodium hydroxide heel at ambient temperature so that the molar ratio: n(HCl)/n(NaOH)=1.

31.3 g of toluene solution are run at ambient temperature, with vigorous stirring (470 rev/min) and over 14 minutes, onto a heel of demineralized water (300.94 g) and of 1N sodium hydroxide (87.24 g). As the reaction is exothermic, the temperature of the medium is controlled using an ice bath. A two-phase medium is obtained. The pH of the aqueous phase is between 6 and 7 (pH paper). 41.99 g of carbon black 2S are then introduced into the medium. The medium is stirred mechanically at AT for 2 h (no exotherm observed).

The contents of the round-bottomed flask are transferred to a pressure filter (filtration on board), along with a toluene fraction (500 ml) used to rinse out the contents of the round-bottomed flask. The black is subsequently dried in an oven (55° C., under 3 mbar) for 15 hours.

The phases are separated and analyzed.

Quantitative determination of iridium results in the following values, collated in Table 3 below:

TABLE 3

| | % Ir | Distribution of iridium/weights |
|---|---|---|
| Aqueous phase | 29-29 ppm | ≈5-5.5% (1) |
| Silicone oil | 560 ppm | ≈5-5.5% (1) |
| Toluene | <10 ppm | |
| Cake | 0.44-0.45% | 80-89% (2) |

(1): Imprecision due to the material balance <100%
(2): Difference due to the accuracy of the quantitative determination of the starting toluene phase.

The efficiency is 84.5% on average.

The capacity of the black for this concentration of 2.94× $10^{-2}$ mol of Ir/kg of black 2S.

The percentages by weight of silicon and of chlorine in the carbon black are as follows:
% Cl: 0.64-0.65
% Si: 0.2-0.3

EXAMPLES 5 AND 6

Recovery of the Iridium by Adsorption with Regard to the Reaction Mixture (Example 5) and with Regard to the Distillation Residue (Example 6)

Either 60 g approximately of reaction medium or 60 g approximately of distillation residue are charged to a fully stirred 100 cc reactor. Stirring is begun and the temperature is maintained at 20° C. Depending on the test, 1 g, 5 g or 10 g of carbon black 3S powder or of sulfonic resins is (are) added. Stirring is maintained for 3 hours.

Subsequently, stirring is halted and the black is filtered off on a Büchner funnel: a liquid phase (filtrate) and a solid phase (black and adsorbed iridium) are recovered. The two phases are analyzed in order to determine the amount of iridium in each phase.

The results are given in the following table:

|  | Weight (g) | [Ir] ppm | Weight of Ir (mg) | Resin (g) | Black (g) | Filtrate Ir (mg) | % Recovered |
|---|---|---|---|---|---|---|---|
| RM | 63.23 | 358 | 22.64 |  | 1 | 3.27 | 85 |
| RM | 57.70 | 358 | 20.66 | 1 |  | 17.56 | 15 |
| Residue | 60.45 | 9400 | 568.23 |  | 1 | 352.00 | 38 |
| Residue | 64.56 | 9400 | 606.86 | 1 |  | 530.00 | 13 |
| RM | 69.00 | 358 | 24.70 |  | 5 | 0.561 | 98 |
| Residue | 69.00 | 9400 | 648.6 |  | 5 | 111.58 | 83 |
| Residue | 62.80 | 10 800 | 677.0 |  | 10 | 15.75 | 97 |

RM: reaction medium; initial iridium charge = 358 ppm by weight.
Residue: distillation residue; initial iridium charge = 9400 to 10 800 ppm by weight.
% Recovered: percentage of iridium recovered on the solid.

EXAMPLE 7

Recovery of Iridium with Carbon Black 3S Powder (Ceca) with Regard to the Distillation Residue 300 g of distillation residue with an iridium content of 9400 ppm by weight are charged to a fully stirred 500 cc reactor. Stirring is begun and the temperature is maintained at 20° C. 23 g of carbon black 3S powder are added. Stirring is maintained for 3 hours.

Subsequently, stirring is halted and the black is filtered off on a Büchner funnel (filtration under vacuum): a liquid phase (filtrate) and a solid phase (black and adsorbed iridium) are recovered. The two phases are analyzed in order to determine the amount of iridium in each phase:

filtrate: concentration of iridium=2500 ppm;

iridium recovered on the black: 80% of the initial charge, i.e. 7520 ppm.

The filtrate recovered (265 g) is reintroduced into the reactor. 20 g of black are added and the mixture is stirred for 3 hours. The solid is subsequently filtered off on a Büchner funnel:

filtrate: concentration of iridium=560 ppm;

iridium recovered on the combined black: 97.3% of the initial charge, i.e. 9150 ppm.

The results obtained are shown in FIG. 1.

EXAMPLE 8

Continuous Recovery of the Iridium with Carbon Black 3S Powder (Ceca) with Regard to the Distillation Residue A fixed bed of carbon black granules is used. The diameter of the bed is 1 cm and the length is 50 cm. The amount of black charged to the bed is 20 g. The hourly flow rate of distillation residue (with a concentration of iridium of 9400 ppm by weight) injected corresponds to 5 times the volume of the bed of carbon black, i.e. a flow rate of 0.2 liter/h.

Under these conditions, the empty tank velocity is 2.5 m/h and the breakthrough time is 10 hours. The amount of residue treated is 2 liters, i.e. 19 grams of iridium involved. The amount of iridium recovered in the fixed bed is 18.7 grams (98.5% recovered).

The capacity of the black in the continuous process is thus 5 mol/kg.

What is claimed is:

1. A process for the preparation of a haloalkyldialkylchlorosilane of formula (I):

$$\text{Hal-}(R^2R^3)\text{Si}—(CH_2)_s\text{-Hal}$$

by the hydrosilylation reaction of a reaction medium comprising a silane of formula (II):

$$\text{Hal-}(R^2R^3)\text{Si}—H$$

and an alkenyl halide of formula (III):

$$CH_2=CH—(CH_2)_{s-2}\text{Hal}$$

in the presence of a catalytically effective amount of a hydrosilylation catalyst based on iridium,
in which formulae:
the symbol Hal represents a halogen atom chosen from chlorine, bromine and iodine atoms,
the symbols $R^2$ and $R^3$, which are identical or different, each represent a monovalent hydrocarbon group chosen from a linear or branched alkyl radical having from 1 to 6 carbon atoms and a phenyl radical, and
s represents an integer between 2 and 10 inclusive,
wherein at the end of the hydrosilylation reaction, the product of formula (I) formed is recovered and the iridium is recovered, said iridium being found in its original form of catalyst or in a converted form, the recovery of said iridium taking place under the following conditions a), b) and c):
a) the recovery of the iridium is carried out:
1. either directly on the reaction medium at the end of the reaction,
2. or on the liquid distillation residue, comprising the byproducts and the iridium or its derivatives, as is obtained after distillation of the reaction medium in order to separate therefrom the product of formula (I),
b) the iridium is recovered by bringing the reaction medium or the distillation residue into contact with an effective amount of carbon black which adsorbs the iridium, and
c) the carbon black is separated from the iridium for the purpose of recovering said iridium.

2. The process as claimed in claim 1, wherein s is equal to 3.

3. The process as claimed in claim 2, wherein the catalyst corresponds to the formula:

$$[Ir(R^4)Hal]_2 \qquad (IV)$$

where:
the symbol $R^4$ represents an unsaturated hydrocarbon ligand comprising at least one C=C double bond and/or at least one C≡C triple bond, it being possible for these unsaturated bonds to be conjugated or non-conjugated, said ligand being linear or cyclic (mono- or polycyclic), having from 4 to 30 carbon atoms, having from 1 to 8 ethylenic and/or acetylenic unsaturations and optionally comprising one or more heteroatoms.

4. The process as claimed in claim 3, wherein the catalyst is chosen from:
di-µ-chloro-bis(divinyltetramethyldisiloxane)diiridium,
di-µ-chloro-bis(η-1,5-hexadiene)diiridium,
di-µ-bromo-bis(η-1,5-hexadiene)diiridium,
di-µ-iodo-bis(η-1,5-hexadiene)diiridium,
di-µ-chloro-bis(η-1,5-cyclooctadiene)diiridium,
di-µ-bromo-bis(η-1,5-cyclooctadiene)diiridium,
di-µ-iodo-bis(η-1,5-cyclooctadiene)diiridium,
di-µ-chloro-bis(η-2,5-norbornadiene)diiridium,
di-µ-bromo-bis(η-2,5-norbornadiene)diiridium, or
di-µ-iodo-bis(η-2,5-norbornadiene)diiridium.

5. The process as claimed in claim 3, wherein the content of catalyst, calculated as weight of catalyst metal, is greater than 30 ppm, calculated with respect to the total weight of the reaction mixture formed by the products of formulae (I), (II) and (III).

6. The process as claimed in claim 1, wherein in the case where the adsorption stage is carried out on the distillation residue, the process additionally comprises, after the stage of distillation of the reaction medium, an additional stage in which the liquid residue is brought into contact with water optionally in the presence of an organic solvent which is inert with regard to HHal formed, for the purposes of obtaining an aqueous phase and an organic phase and of hydrolyzing said residue.

7. The process as claimed in claim 6, wherein the water is added in an amount sufficient for the HHal formed not to be at saturation in the aqueous phase.

8. The process as claimed in claim 1, wherein the product of formula (I) is 3-chloropropyldimethylchlorosilane, the product of formula (II) is dimethylhydrochlorosilane and the product of formula (III) is allyl chloride.

9. The process as claimed in claim 1, wherein the adsorption is carried out batchwise by bringing the carbon black of powder or granule type into contact with the reaction medium or the distillation residue.

10. The process as claimed in claim 1, wherein the adsorption is carried out continuously by bringing carbon black present in a column or a fixed bed or a cartridge into contact with the reaction mixture or the distillation residue.

* * * * *